United States Patent [19]

Lenkauskas

[11] Patent Number: 4,624,672
[45] Date of Patent: Nov. 25, 1986

[54] COILED WIRE PROSTHESIS FOR COMPLETE OR PARTIAL OSSICULAR RECONSTRUCTION

[76] Inventor: Edmundas Lenkauskas, 3024 Kersdale Rd., Pepper Pike, Ohio 44124

[21] Appl. No.: 589,709

[22] Filed: Mar. 15, 1984

[51] Int. Cl.$^4$ .............................................. A61F 2/18
[52] U.S. Cl. ..................................... 623/10; 128/1 R
[58] Field of Search ................... 128/1 R, 92 C; 3/1, 3/1.4, 1.9

[56] References Cited

U.S. PATENT DOCUMENTS

| | | | |
|---|---|---|---|
| 3,710,399 | 1/1973 | Hurst | 3/1 |
| 3,913,587 | 10/1975 | Newash | 3/1 |
| 4,041,931 | 8/1977 | Elliott et al. | 3/1.4 |

*Primary Examiner*—Richard J. Apley
*Assistant Examiner*—David Isabella
*Attorney, Agent, or Firm*—Vytas R. Matas

[57] ABSTRACT

A stainless steel wire prosthesis C and P is provided for reconstruction of sound conducting mechanism in the middle ear. The prosthesis C and P is able to compensate for outward retraction and shift of the tympanic membrane occurring during the healing process and which is able to supress loud noise from damaging the inner ear. To accomplish this the prosthesis C and P has a spring coil (10) located between a pair of arms (14) and (16) at angular separation oriented to be aligned with the tympanic membrane and the oval window or stapes respectively. Because of this the spring coil has a non-linear spring constant and thus maintains a substantially constant tension pressure through the stapes footplate of the inner ear even with orientation changes between the tympanic membrane and the footplate. The spring coil (10) also acts as a shock absorber for any external trauma on the tympanic membrane.

19 Claims, 7 Drawing Figures

COILED WIRE PROSTHESIS FOR COMPLETE OR PARTIAL OSSICULAR RECONSTRUCTION

BACKGROUND OF THE INVENTION

1. Field of the Invention

The present invention relates to otic prosthesis in general and in particular to a middle ear prosthesis used in both complete and partial ossicular repair.

2. Description of the Prior Art

It is presently known to repair the sound conducting mechanism of the middle ear by surgical implantation of various types of prosthesis. Such repair may involve either complete or partial reconstruction replacement of all three ossicles between the tympanic membrane of the outer ear and the oval window of the inner ear.

The three ossicles include the malleus, the incus, and the stapes. When only the malleus and the incus are removed with the stapes being left intact, the prosthesis need span only the space between the tympanic membrane and the superstructures of the stapes, mainly the capitulum (stapes head). This is generally referred to as a partial ossicular reconstruction procedure. When the stapes superstructures are removed along with the malleus and incus the prosthesis spans the entire space between the tympanic membrane and the stapes footplate and is generally referred to as a complete ossicular reconstruction procedure.

Known prior art prosthesis for both complete and partial reconstruction procedures have been made from various natural materials such as cartilage and bone, and from various man-made materials such as stainless steel and plastics like Teflon, Polyethelene, and biocompatible materials like Proplast and Plastipore. New ceramics are also being developed.

Irrespective of the material the prosthetic devices known are usually one piece straight shaft devices having a head portion resting against the tympanic membrane with the opposite end pressing against the footplate of the stapes in complete reconstruction procedures or the stapes capitulum-superstructure in partial reconstruction procedures.

For a discussion of prior art prosthetic devices and the implanting techniques of same, the reader is referred to the following articles which discuss such devices in greater detail. These articles are "A DECADE OF TYMPANOPLASTY: PROGRESS OR REGRESS?" by David F. Austin, M.D. appearing in the May 1982 Issue of Larynogoscope 92: "BIO COMPATIBLE OSSICULAR IMPLANTS" by John J. Shea, M.D. and John R. Emmett, M.D. appearing in Volume 104, April 1978, Issue of Arch. Otolaryngol. and "OSSICULAR CHAIN RECONSTRUCTION: THE TORP AND PORP AND CHRONIC EAR DISEASE" by C. Gary Jackson, M.D. et.al. appearing in the Aug. 1983 Issue of Larynogoscope.

Wire prosthetic devices are also known. However, such devices consist of a straight shaft stainless steel wire with a transverse bar located at one end of the wire shaft. The bar or any other transverse section is intended to limit the insertion of the device into any base material located under the tympanic membrane. All straight shaft prosthetic devices give rise to certain problems due to their lack of flexibility such as a slight outward retraction and/or shift of the tympanic membrane which may occur during the post-operative healing process. This outward retraction causes the tip of the prosthetic device to lift off from either the footplate or stapes head, depending upon the type of reconstruction, resulting in a loss of the tension pressure between the tympanic membrane and the footplate that was initially set by the surgeon implanting the prosthetic device. Thus the patient does not hear as well after the healing from the operation as he did when the operation was just performed. In situations where the ear is subjected to a loud noise, the extreme deflection of the tympanic membrane caused by the noise may damage the inner ear—the cochlea. Also, there is no protection for inner ear damage from external physical trauma to the ear.

Thus it is seen that a prosthetic device is required which would provide flexibility to absorb shocks induced by loud noises or other external trauma to the ear and which would have sufficient flexibility to compensate for any displacement change between the tympanic membrane and the inner ear due to outward retraction and/or shift occurring during the post operative healing process to maintain sufficient pressure between them to insure adequate hearing restoration over an extended period of time.

SUMMARY OF THE INVENTION

The present invention overcomes the mentioned problems associated with the known prior art devices as well as others by providing a flexible coiled wire prosthetic device useful for both complete and partial ossicular replacement procedures. The device is formed from wire to have at least one coil assembly along the length of the device with arms extending at an angle from this coil assembly. The arms form an angular separation of approximately 90 degrees or less. The coil assembly is formed in a plane substantially perpendicular to the plane of the arms of the device.

In one particular embodiment of the device, at one end of the upper arm of the prosthesis is the prosthesis head. A protruding tip of the wire from it is cut at an angle to provide a sharp point for easy penetration into any base material used to cover a part of the undersurface of the tympanic membrane in the reconstruction procedure. The base material is usually cartilage or cortical plate connected or mounted against the tympanic membrane to prevent an extrusion of the prosthesis. At the other end, at the end of the leg of the device there is a small loop which has a similar shorter angularly cut sharp end for fixing that leg of the device on the footplate of the stapes in complete ossicular replacements.

In view of the foregoing it will be seen that one aspect of the applicant's invention is to provide a flexible coiled wire prosthesis for ossicular replacement which would maintain a predetermined pressure between the tympanic membrane and the inner ear during any short or long term realignments between the tympanic membrane and the inner ear.

Another aspect of the applicant's present invention is to provide a coiled wire prosthesis which would compensate for outward retractions and/or shifts of the tympanic membrane which may occur during the healing process.

Yet another aspect of the applicant's present invention is to provide noise protection of the inner ear from both sound trauma and external physical trauma to the ear such as barotrauma.

Yet one other aspect of the applicant's present invention is to provide a stainless steel wire otic prosthesis which is not subject to adhesions, tissue reaction or deterioration.

These and other aspects of the applicant's present invention will become more apparent upon a review of the following description of the preferred embodiment when considered in conjunction with the accompanying drawings.

DESCRIPTION OF THE PREFERRED EMBODIMENT

Figure 1:
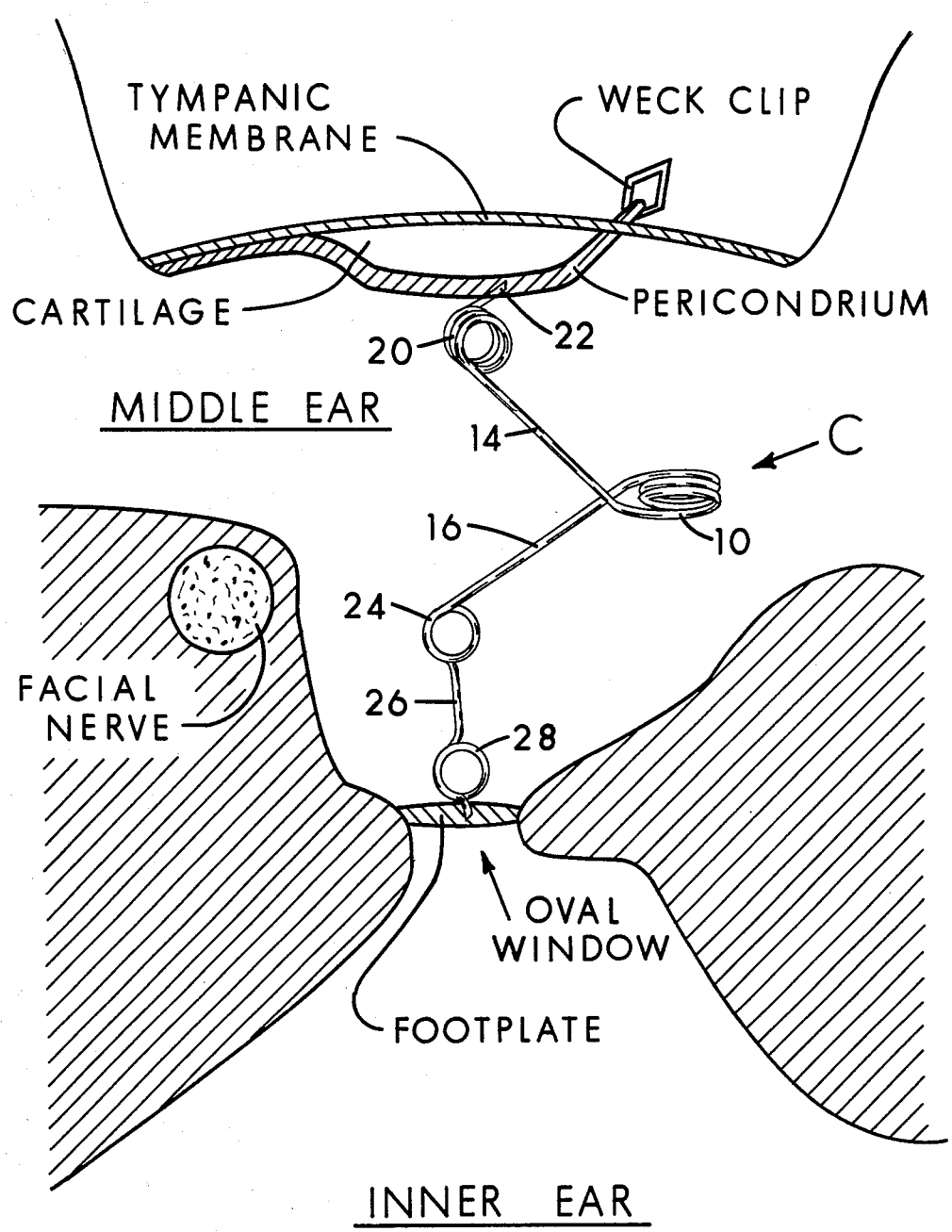
FIG. 1 shows one form of a wire coil prosthesis of the present invention surgically placed between the tympanic membrane and the footplate of the stapes forming a complete ossicular replacement.

Referring now to the drawings, it will be understood that the showings therein are intended to teach a preferred embodiment of the present invention but are not intended to limit the invention thereto.

Figure 3:
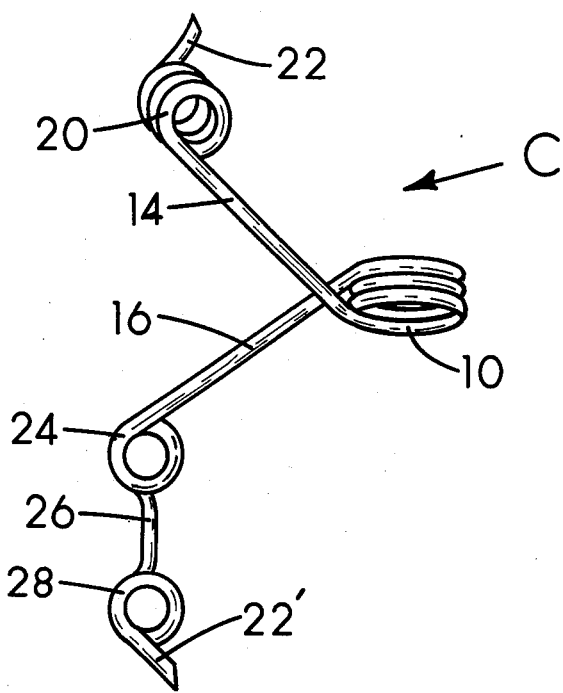
FIG. 3 is an expanded side view of one form of the FIG. 1 prosthesis.

As best seen in FIGS. 1 and 3 a wire spring prosthesis assembly C is shown surgically placed between the tympanic membrane and the stapes footplate in a manner which will be described later. This type of surgical implantation is known as complete ossicular replacement and is done where the malleus, incus and stapes of the ear require replacement.

The prosthesis assembly C is formed from a stainless steel wire having a diameter of 0.005 inches and a chemical composition by fraction of total weight as indicated in the following table. This table lists the composition by weight of the various alloy forming materials under the block having the material identified at the top of the block. The total weight of the sample wire is 35.813 grams.

| C | Mn | P | S | Si | Cr | Ni | Mo | Zr | Se |
|---|---|---|---|---|---|---|---|---|---|
| .015 | 1.78 | .020 | .004 | .39 | 17.40 | 13.72 | 2.17 | | |

| Ti | Cb/Ta | Al | N | Cu | Co |
|---|---|---|---|---|---|
| | | | .034 | .17 | .11 |

The prosthesis assembly C has a triple loop coil assembly 10 formed from the described stainless steel wire into a diameter of approximately 1½ mm. Extending from the triple loop coil assembly 10 is a short upper arm 14 alignable with the prosthesis head and a long lower arm 16 alignable with a leg 26. The extension and separation of the arm 14 and 16 and the leg 26 are designed to provide terminations coinciding with the physical alignments of the tympanic membrane and the footplate to insure the extended retention therebetween.

At the end of the short upper arm 14 of the assembly C is a coiled head of the prosthesis consisting of a triple coil 20 approximately 1 mm in diameter having a slight wire tip protrusion 22 extending from the triple coil 20. This extending point 22 is cut at an angle to provide a sharp end for easy piercing into carilages perichondrium or other base material located beneath the tympanic membrane during the implantation operation.

The longer arm 16 has a loop 24 formed at the end thereof with the prosthesis leg 26 extending from the loop 24. The end of the prosthesis leg 26 is a loop 28 with a slightly protruding angle cut wire tip to allow for fixation of the prosthesis on the footplate. The loop 24 is used to fascilitate the surgical implantation of the prosthesis assembly C in a manner that will be described later.

The triple loop coil assembly 10 is wound in a plane which is perpendicular to the plane locating the arms 14 and 16. This type of plane orientation along with the indicated leg separation was found to give the prosthesis assembly C a non-linear spring rate. Thus it was found that whereas 3 grams caused a 1 mm. compression of the prosthesis assembly C 4 grams caused a 2 mm. compression of the prosthesis assembly C. The orientation of the triple loop coil assembly 10 may be in the same plane as the arms 14 and 16. However, this orientation did not produce the same non-linear spring rate, but such a construction could be used. It was felt that the prosthesis assembly C provided for easier surgical implantation and wider functional use for the prosthesis as well as better protection from external trauma to the inner ear. The non-linear spring constant provides less undesired extra pressure to the footplate in cases of collapsing tympanic membranes.

Figure 4:
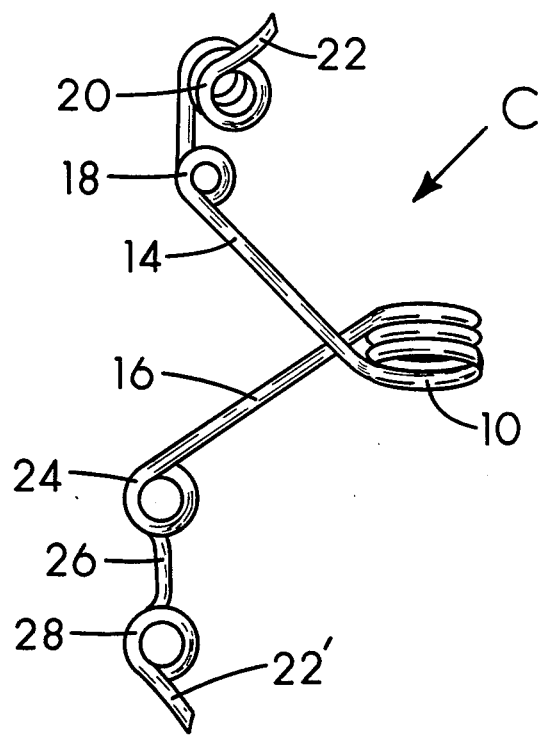
FIG. 4 is an expanded side view of a second form of the FIG. 1 prosthesis having an extension loop on the upper arm under the head of the prosthesis.

Clearly the spacing and orientation between the tympanic membrane and the footplate will vary depending on the anatomical variation and surgical procedures affecting the level of the tympanic membrane. To this end the leg 26 of the prosthesis C is made in two lengths. Further compensation for these mentioned differences is made available in the FIG. 4 embodiment of the main prosthesis assembly C. The same numbers as in FIG. 3 have been maintained in the FIG. 4, 5 and 6 embodiments for like parts. An extension coil 18 is shown located on the upper arm 14 proximate to the head coil 20. The purpose of this coil 18 is to allow the physician performing the implantation to extend the length of the short arm 14 by stretching the coil 18.

Figure 2:
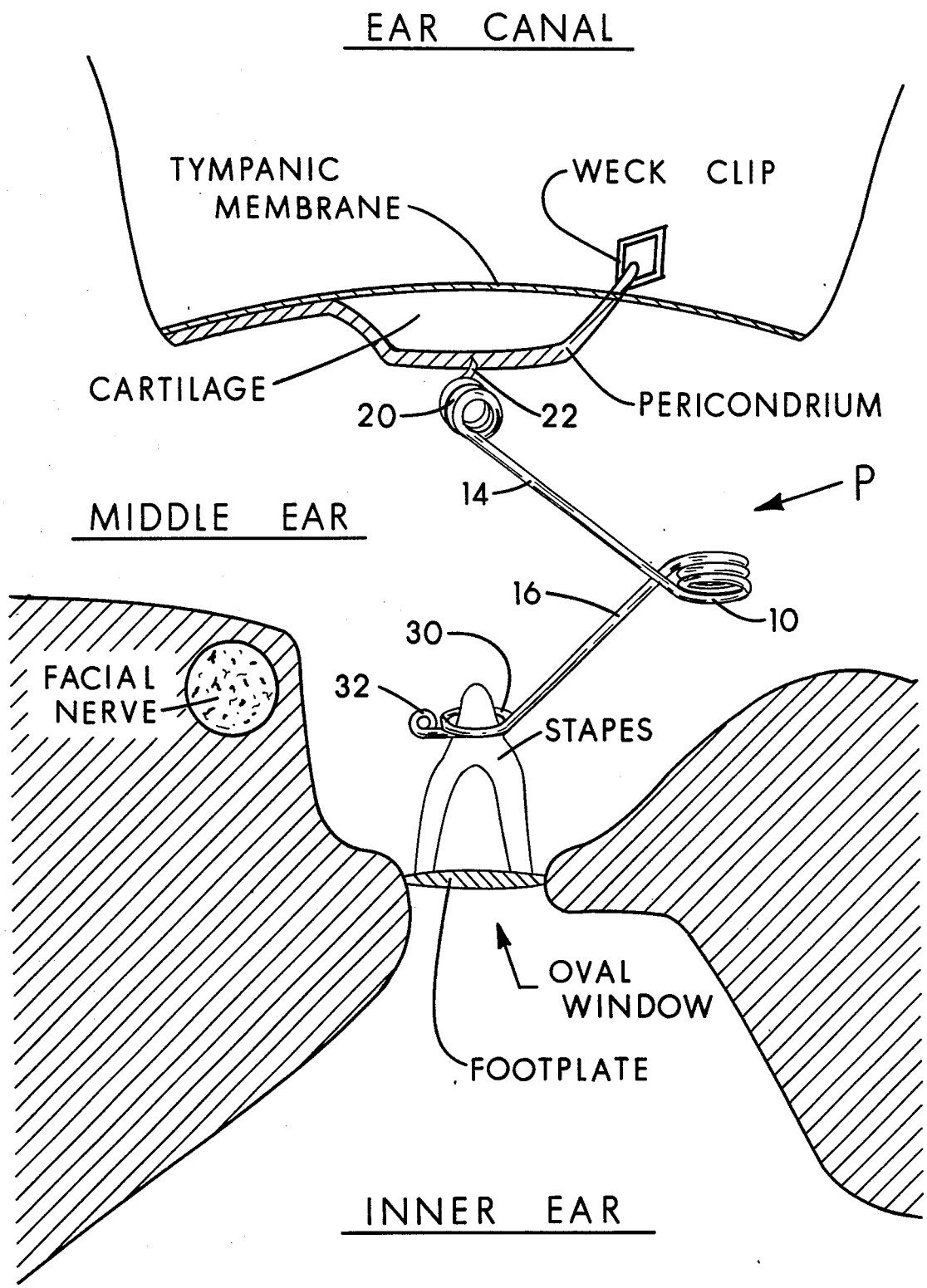
FIG. 2 shows another form of a wire coil prosthesis of the present invention surgically placed between the tympanic membrane and the stapes superstructure forming a partial ossicular replacement.
Figure 5:
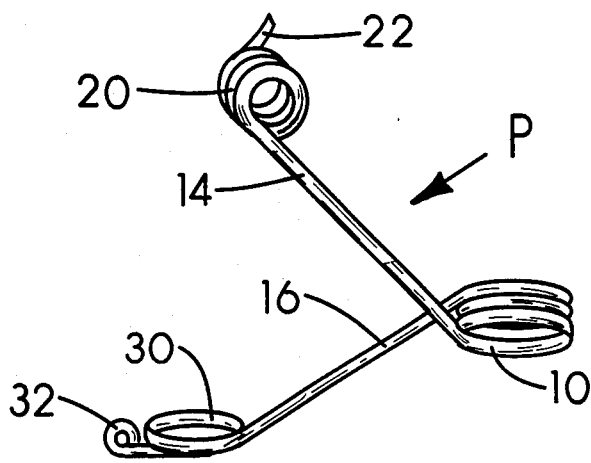
FIG. 5 is an expanded side view of one form of the FIG. 2 prosthesis.

In FIG. 2 and 5 a prosthesis assembly P is shown surgically placed for a partial reconstruction and is similar to the FIG. 1, and 3, prosthesis assembly C both in numbering of like parts, material composition and formulation with the exception that the extension leg 26 and the loop 24 is replaced by an oval loop 30 of approximately 1½ mm. in a longer diameter located in the same plane as the triple coil spring assembly 10. This difference in structure is needed to secure the prosthesis assembly P over the superstructure of the stapes by setting the loop 30 around the stapes head. At the end of the oval loop 30 there is a small loop 32 to fascilitate the surgical implantation of the oval loop 30 over the stapes head.

To surgically place the prosthesis assembly C or P, the middle ear is first entered by making a small endaural incision and raising the skin flap from the posterior ear canal. The raised skin flap with the posterior part of the tympanic membrane exposes the middle ear where either the oval window with the stapes is present or in the situation requiring complete ossicular replacement, only the footplate of the stapes remains in the oval window. A suitable size of coil spring prosthesis C or P is then chosen to fit the space between the stepedial footplate and the tympanic membrane or the stapes superstructures and the tympanic membrane. Next a longitudinal strip of cartilage disk is dissected with the perichondrium (the skin of the cartilage) located on one side thereof. This strip could be formed as a disk. This strip is dissected from the cartilage at the anterior edge of the endaural incision. The removed strip of the cartilage is removed with the perichondrium, (the skin of the cartilage). This strip of cartilage is then prepared by removing a part of the cartilage from both ends of the strip leaving a disc of 3-4 mm in diameter attached to the perichondrium. The strips of perichondrium extend from the cartilagenous disc in both directions. Then a small incision is made in the tympanic membrane for better fixation of that cartilagenous disc which is brought into the middle ear under the tympanic membrane and the shorter perichondrium end retained with neck chips. The chosen size coil spring prosthesis assembly C or P is then brought into the middle ear with the coil assembly 10 facing forward toward the eustachien tube (not shown). The short sharp tip 22 extending from the triple loop coil 20 is stuck into the perichondrium at the center of the cartilagenous disc under the tympanic membrane. Then a right angle pick is introduced into the loop 24. By lifting and flexing the prosthesis assembly C the leg 26 of the prosthesis assembly C is transported into the oval window over the center of the footplate. When in place the prosthesis assembly is compressed approximately 1 mm. Since the procedure is done under a local anesthesia the hearing is then tested to confirm a good connection between the tympanic membrane and the footplate. The ear canal is packed and the ear is closed in a usual manner.

Figure 6:
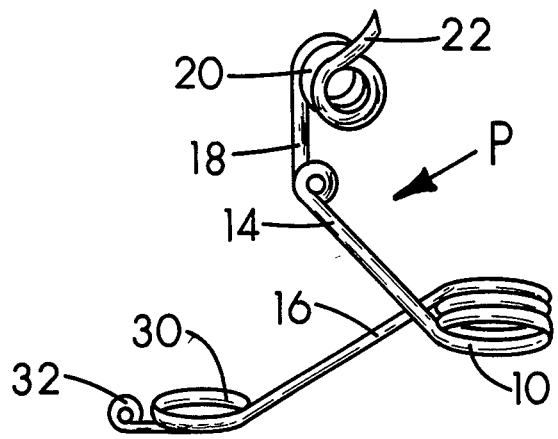
FIG. 6 is an expanded side view of a second form of the FIG. 2 prosthesis having an extension loop on the upper arm.
Figure 7:
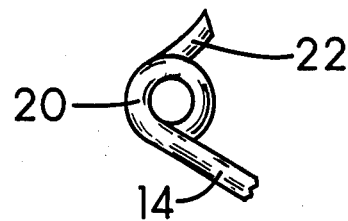
FIG. 7 is an expanded side view of the prosthesis' head at the end of the upper arm of FIGS. 3 through 6 showing the protruding tip of the wire cut an an angle.

The operative procedure for insertion of the FIG. 2, 5 and 6 replacement prosthesis assembly P for partial replacement is the same as previously described for complete replacement with only one small deviation. In this deviation the oval loop 30 at the end of the arm 16 is brought over the head (capitulum) of the stapes using a right angle pick inserted into the loop 32 instead of the placement of the coil 28 against the footplate. Since the oval loop 30 is set over the head of the stapes or around the neck of stapes its planar orientation is perpendicular to that of the coil 28.

From the foregoing it will be seen that once the prosthesis is in place any displacement of the tympanic membrane from any type of external trauma would be absorbed by the coiled assembly 10 of the prosthesis assembly C without resulting in an extrusion through the oval window into the inner ear, or fracturing the crura of the stapes when the partial prosthesis assembly P is used. Any space reorientation due to healing would be compensated by the coil assembly 10 which as indicated earlier has a non-linear spring constant and thus maintains substantially the same functional range of tension pressure for moderate space variations. It will be recalled that 3 grams compressed the assembly 10 1 mm. and 4 grams compressed the assembly 2 mm. Similarly even after healing if the ear is subjected to any external trauma pressure such as barotrauma (trauma due to barometric pressure differences) the prosthesis assembly C or P is easily compressed and of course, springs back to its normal pressure retention between the tympanic membrane and the oval window. The displacement of the tympanic membrane due to excessive loud noise is in great part absorbed by the coil element 10 which substitutes for the built-in protective mechanism in the normal middle ear for that purpose. The normal transfer of sound is not significantly affected by the coil spring assembly 10.

Certain modifications and improvements have been deleted herein for the sake of conciseness and readability but are clearly intended to fall within the scope of the following claims. As an example, known surgical base material such as wire mesh could be added to the head of the prosthesis and the prosthesis implanted as a unit under the tympanic membrane.

I claim:

1. A prosthesis for conducting sound between the tympanic membrane and the inner ear comprising:
   an upper arm having a head ring with a sharp point at one end for connecting the upper arm to the tympanic membrane to allow sound vibrations to be conducted from the tympanic membrane through the upper arm;
   a spring coil assembly located at an end of said upper arm opposite the head ring end to facilitate spring action and to conduct sound therealong; and
   a lower arm having one end connected to said spring coil assembly and a second end for conducting sound from said spring coil assembly to the inner ear.

2. A prosthesis as set forth in claim 1 wherein said spring coil assembly is a coil having a series of loops oriented to the upper and lower arm to give the prosthesis a non-linear spring constant.

3. A prosthesis as set forth in claim 1 wherein said spring coil assembly is formed as a ring in a plane substantially perpendicular to a plane containing said upper and lower arms.

4. A prosthesis as set forth in claim 3 wherein said coil assembly is formed as three continuous rings of approximately constant diameter.

5. A prosthesis as set forth in claim 1 including a head coil assembly located at the end of the upper arm opposite said spring coil assembly having a sharp member extending therefrom for retaining said prosthesis in physical contact with the tympanic membrane.

6. A prosthesis as set forth in claim 5 wherein said head coil assembly has three spaced rings for limiting the penetration of the sharp member extending from said head coil assembly.

7. A prosthesis as set forth in claim 5 including an extension coil located along said upper arm proximate to said head coil assembly.

8. A prosthesis as set forth in claim 1 wherein the ear has an intact stapes and wherein said lower arm has a oval loop formed at the end for mounting to said stapes.

9. A prosthesis as set forth in claim 8 wherein said oval loop of said lower arm is formed in the same plane as the plane of said spring coil assembly.

10. A prosthesis as set forth in claim 1 wherein the middle ear structure has a footplate and wherein said leg has a loop at the end thereof extending therefrom to the said footplate.

11. A wire prosthesis device for replacing middle ear structure located between the tympanic membrane and the inner ear comprising:

a first section of the wire device device formed as a straight arm portion;

a second section of the wire device being formed as a spring coil at the end of the straight arm portion of said first section;

a third portion of the wire device being formed as a lower arm portion extending from the spring coil of said second section of the wire device; and wherein the spring coil of said section of the wire device is perpendicular to said first section and said third portion of the device.

12. A wire prosthetic device as set forth in claim 11 wherein the wire is a stainless steel alloy.

13. A wire prosthetic device as set forth in claim 12 wherein the wire is approximately 0.005 inch diameter.

14. A wire prosthetic device as set forth in claim 11 wherein the spring coil is formed as three continuous loops of approximately identical diameter.

15. A wire prosthetic device as set forth in claim 11 wherein said spring coil is formed to allow compression of the arms of the device approximately 1 mm. upon the subjecting of 3 grams of force to the device and to compress the arm of the device approximately 2 mm., upon the subjecting of 4 grams of force to the device.

16. A wire prosthetic device as set forth in claim 11 including extension means formed on the wire device for varying the lengths of a section of the wire device.

17. A wire prosthetic device as set forth in claim 16 wherein said extension means is formed as a coil on the upper arm of said section of said wire device.

18. A method of surgically placing a spring wire prosthesis having a pair of arm sections extending from a coil spring into the middle ear between the tympanic membrane and the inner ear complex comprising the steps of:

placing a base material under the tympanic membrane of a cartilage disc material against the undersurface of the tympanic membrane with the perichondrium covering the cartilage facing the middle ear space, pressing the head of the prosthesis at the end of the upper arm of the spring wire prosthesis into the perichondrium to connect one end of the prosthesis to the tympanic membrane thereby; and connecting the leg section of the prosthesis to the stapes footplate in the oval window to provide a coupling of the tympanic membrane to the inner ear complex thereby.

19. A method as set forth in claim 18 where the middle ear has a stapes structure intact and wherein the prosthesis has an oval loop section at the end of the lower arm and wherein the step of connecting the lower arm section of the prosthesis to the inner ear complex includes the step of setting the oval loop section on the superstructures of the stapes.

* * * * *